United States Patent
Baker et al.

(10) Patent No.: US 7,297,962 B2
(45) Date of Patent: *Nov. 20, 2007

(54) METHOD FOR PERFORMING SPACIALLY COORDINATED HIGH SPEED FLUOROMETRIC MEASUREMENTS

(75) Inventors: Glenn Baker, Edison, NJ (US);
Salvatore H. Atzeni, Edison, NJ (US);
James R. Mattheis, Edison, NJ (US);
Raymond Kaminski, Edison, NJ (US)

(73) Assignee: Horiba Jobin Yvon, Inc., Edison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/184,721

(22) Filed: Jul. 19, 2005

(65) Prior Publication Data

US 2006/0017921 A1   Jan. 26, 2006

Related U.S. Application Data

(63) Continuation-in-part of application No. 10/763,681, filed on Jan. 23, 2004.

(60) Provisional application No. 60/442,036, filed on Jan. 23, 2003.

(51) Int. Cl.
*G01N 21/62* (2006.01)
*G01N 21/64* (2006.01)

(52) U.S. Cl. ............................ 250/458.1; 250/459.1; 356/317; 356/318

(58) Field of Classification Search ............ 250/201.3, 250/458.1, 459.1; 356/317, 318, 417
See application file for complete search history.

(56) References Cited

U.S. PATENT DOCUMENTS

| | | | |
|---|---|---|---|
| 5,865,754 A * | 2/1999 | Sevick-Muraca et al. | ... 600/476 |
| 6,496,267 B1 * | 12/2002 | Takaoka | ...................... 356/497 |
| 6,741,346 B1 * | 5/2004 | Gerstner et al. | ............. 356/318 |
| 2002/0072677 A1 * | 6/2002 | Sevick-Muraca et al. | ... 600/473 |
| 2004/0156053 A1 * | 8/2004 | Wolleschensky et al. | ... 356/485 |

* cited by examiner

*Primary Examiner*—Davienne Monbleau
(74) *Attorney, Agent, or Firm*—Anthony H. Handal; Brown Rudnick Berlack Israels LLP

(57) ABSTRACT

An optical imager, such as a microscope for performing multiple frequency fluorometric measurements comprising a light source, such as a laser source is disclosed. The system is used to excite a sample into the fluorescent state. Light from the excited sample is collected by a microscope. The microscope utilizes conventional confocal optics optimized to have a very narrow depth of field, thus limiting the information collected to a thin planar region. Measurements are taken over the fluorescence lifetime of the sample simultaneously from the excitation source and from the excited sample. Information is taken in a matrix and comparison of the image matrix and the standard during simultaneous measurements yields output information.

19 Claims, 6 Drawing Sheets

METHOD FOR PERFORMING SPACIALLY COORDINATED HIGH SPEED FLUOROMETRIC MEASUREMENTS

CROSS REFERENCE TO RELATED APPLICATIONS

This application is a CIP Ser. No. of 10/763,681 filed Jan. 23, 2004 which is a non provisional application claiming the priority of prior applications 60/442,036 filed Jan. 23, 2003. The priority of the above application is hereby claimed by the applicant.

TECHNICAL FIELD

The present invention relates to the field of fluorescence and phosphorescence frequency domain measurement using light modulated in intensity with a plurality of frequencies.

BACKGROUND

The characteristics of light emanating from an object or a material may be advantageously detected and analyzed in order to determine characteristics of the object or material under examination. For many years, spectrographic techniques have been used to perform analysis of materials ranging from human blood and other biological materials to slag from a crucible. For example, it has been known that wavelengths of light absorbed by a material, as well as the wavelengths of light emitted by a material during an excited state, such as combustion, both indicate the composition of the material. Today, analytic instruments in industrial, scientific and medical applications make widespread use of such emission spectra and absorption spectra. Another such technique is Raman spectroscopy, where, for example, the output of a mercury vapor arc may be filtered and used to excite a transparent material. As the light transmits through the material, it is scattered and undergoes a change in wavelength and a random alteration in phase due to changes in the rotational or vibrational energy of the sample. Raman scattering is a principal analytic tool in industry and science today.

Another class of analytic instruments uses fluorescence to identify materials. In such systems, an excitation source, such as a laser, is used to excite atoms or molecules, raising electrons into higher energy states. When the electrons revert back to the unexcited state, they fluoresce or emit photons of light characteristic of the excited atom or molecule. In addition, the time delay between the exciting light and the emitted light, as well as the amplitude of the emitted light, provide information about the material's composition, lifetimes, and concentration of various components. Instruments that provide this function are known as frequency domain fluorometers.

While one may now visualize a system in which the excitation source is being modified at incrementally changing rates while simultaneously the corresponding emission spectra is being measured and analyzed over time, in practice, such measurements are achieved by modulating a light source. For example, one may employ for this purpose a pulsed dye laser, or a continuous wave laser whose output is externally modulated by a Pockels cell or an LED which is intrinsically modulated. However, it is anticipated that almost any light source which can be either modulated or pulsed may be employed to implement the invention.

BRIEF SUMMARY OF THE INVENTION

The inventive method of spectrographic measurement may be employed to improve the speed of data collection for the purpose of spatially coordinating the observation of physiological interactions to external stimuli. The inventive method of spectrographic measurement may also be used to improve the speed of data collection for the purpose of spatially coordinating the observation of physiological interactions to external stimuli. In particular a frequency domain fluorometer comprising an excitation source composed of multiple coherent harmonic modulation frequencies coupled with a two-dimensional array detector, may be employed for the purpose of rapid and simultaneous collection of lifetimes over a large sample area.

In particular a frequency domain fluorometer comprising an excitation source composed of multiple coherent harmonic modulation frequencies coupled with a two-dimensional array detector may be used for the purpose of rapid and simultaneous collection of lifetimes over a large sample area.

By "phase" is meant the re-emission delay in degrees or time, of the modulated fluorescence emission of an unknown sample as compared to a modulated reference, which may be either the excitation source or a known sample. By "modulation", sometimes also referred to as the modulation ratio, is meant the ratio of the amplitude of a fixed reference, either a known sample or the excitation source, to the fluorescence amplitude of the unknown sample. A further refinement of the measurement technique is to perform the measurement of modulation and phase on a sample many times using different modulation frequencies each time. Generally, this results in the generation of a first characteristic for phase as a function of modulation frequency and a second characteristic of modulation as a function of modulation frequency. Generally, phase angle will increase with increasing modulation frequency. Moreover, for samples exhibiting longer lifetimes, phase will be larger at a given modulation. Similarly, modulation tends to decrease for samples exhibiting longer lifetimes, at a given modulation frequency.

If curve fitting techniques are used to match the plot of frequency versus phase and the plot of frequency versus modulation, to a pair of equations, analysis of the equations can be used to discern multiple individual fluorescing components, for example organic molecules, fluorescing semiconductor depositions or dopants or the like, in a sample. Curve fitting techniques are known in the field today and generally involve the use of a digital computer to perform the desired curve fitting and the comparison of various physical models that represent the molecular system and its environment.

Frequency domain cross-correlation techniques are well developed in the prior art (e.g. 4,840,485, 5,151,869, 5,196,709 etc.) and commercial instruments are available for sale. The downside of these techniques are that each frequency is individually scanned, and this is a slow process. Additionally only one detector at a time is used, and one loses any spatial relationships within the samples.

To maintain the spatial relationships with the sample another technique has been developed and is implemented as a fluorescence lifetime imaging microscope (FLIM), using a single frequency domain instrument coupled to a camera using homodyne and sometimes heterodyned detection.

A further improvement on these technique was disclosed and patented by Mitchell in U.S. Pat. No. 4,937,457. Mitchell disclosed a technique of producing multiple coherent harmonics to speed up the process of data collection.

In accordance with the invention, multiple frequencies and two-dimensional detectors are combined to speed data collection (mff) for the purpose of spatially coordinating 2D (i.e. two dimensional) detection.

The term "speed" as used herein refers to the collection of multiple channels and multiple frequencies simultaneously. The term also refers to the rapid collection of data on each frequency.

In accordance with the invention, it has been recognized that the identification of multiple components in certain types of samples can be facilitated through the association of spatial data with optical readings. This may be achieved through the use of a fluorescence detector having a plurality of elements. In accordance with the invention, different points on a sample produce fluorescence emissions which are measured by separate fluorescence detector elements. Accordingly, it is possible to measure a particular effect with respect to different parts of the sample.

More particularly, in accordance with the invention, a light source, such as a laser source, is used to excite a sample into the fluorescent state. Light from the excited sample is collected by a microscope. The microscope utilizes conventional confocal optics optimized to have a very narrow depth of field, thus limiting the information collected to a thin planar region.

It will be understood to those of skill in the art that a microscope is only one way to get image (spatial) data. The inventive system may be employed in connection with any suitable image generation system. While the term image is used in connection with the inventive system, it is noted that the invention is generally applicable to measurement systems having data inputs which are spatially mapped, and which may never be assembled to form an image in the conventional sense of the term. However, such spatially mapped data may be processed, for example, in a computer, in a manner resembling the processing of an image by the eye. Alternatively, various selection criteria may be implemented in the processing of the mapped data.

In accordance with the invention, an image in two dimensions of a planar region may be focused on the sensitive input face of an image intensifier. The image intensifier, at its output, presents an amplified optical image of the thin planar region. This amplified optical image then drives, for example, two dimensional array detector such as a CCD (charge-coupled device), CMOS array, or other array detectors. Alternatively, the inventive method may be implemented without an image intensifier.

The CCD array detector outputs what may be understood as a two-dimensional matrix of information respecting the fluorescence characteristics of the various parts of the sample.

The same can be achieved by the following three methods using the heterodyned modulation:
1. Modulating the image intensifier;
2. Modulating the gain of the array detector; or
3. Mixing the output of the array detector with a heterodyn signal.

It is important to note that, the information obtainable is not limited to amplitudes (as alluded to above) but also the lifetime of desired parameters in model space, which can be graphically displayed as two-dimensional or three-dimensional data. Such an energy level display may be useful standing alone. However, the display may have superimposed on the energy level display a graphical indication of the parts of the image. Such a graphical indication may be generated by simple image display or may be enhanced using artificial intelligence or other computer techniques, such as boundary detection and other well-known imaging techniques. Such information can be sent to an imaging device and the imaging information superimposed on the matrix of information.

Using such techniques, and computer implemented pattern analysis techniques, a wide variety of information may be obtained. For example, rotation may be measured. Moreover, because such measurement is based on image data, such information can be generated in greater detail than that obtainable using conventional techniques.

A method of spectrographic measurement comprises generating a plurality of modulation signals at a plurality of modulation frequencies the modulation signals to an excitation source. The excitation source produces excitation light for illuminating a sample to be assayed. The modulation signals vary the amplitude of the excitation light by modulating the excitation light with the plurality of modulation signals. A portion of the excitation light which has been varied in amplitude is sampled to form a reference optical excitation signal. The sample to be assayed is illuminated with the excitation light, causing the sample to emit an output optical signal. The output optical signal is imagined on a multielement optical detector having a plurality of elements, whereby each of the elements is associated with a region on the sample to be assayed. A plurality of measurement signals is generated using the multielement optical detector. Each measurement signal is associated with a single one of the elements. A plurality of heterodyne signals are generated at a plurality of heterodyne frequencies. Each of the heterodyne frequencies are associated with one of the modulation frequencies. For each measurement signal associated with an element of the multielement optical detector, the measurement signal are mixed with the heterodyne signals to generate a plurality of low-frequency measurement modulation products. One low-frequency measurement modulation product is associated with each of the modulation frequencies and comprises the difference between a single modulation products is associated with one of the low-frequency measurement modulation products. For each of the plurality of low-frequency measurement modulation products, the low-frequency measurement modulation product is compared to its associated reference modulation product to generate an output signal indicating characteristics of the sample at the region on the sample associated with each of the elements. The comparison is done by measuring the relative phase and amplitude of the low-frequency measurement modulation product as compared to the reference modulation product and generating a modulation data point and a phase data point. For each element, the modulation data points are fitted to a first curve using the method of least squares. For each element the phase data points are fitted to a second curve using the method of least squares.

The first and second curves are compared to a database to determine characteristics of the sample and the characteristics are displayed. The system is calibrated by first using, in place of the sample, a standard consisting of a zero lifetime scattering solution to create a set of normalizing phase and modulation standard values against which the phase and modulation values for the sample are measured.

The modulation and heterodyne signals may be logarithmically related. The modulation signals may be incoherent. The modulation signals may be out of phase with each other. The excitation light may be generated with a laser. The output optical signal may comprise fluorescent or phosphorescent energy from the sample. The modulation frequencies may be selected to have a high root mean square value. The excitation source may be a laser and the excitation light may be modulated by a Pockel's cell. The excitation source may be a laser whose output is a pulsed laser output. The laser may be a pulsed-dye laser.

BRIEF DESCRIPTION OF THE DRAWINGS

The advantages, and a method and apparatus for implementing the present invention will be understood from the following description taken together with the drawings, in which.

DETAILED DESCRIPTION OF THE BEST MODE OF THE INVENTION

Figure 1:
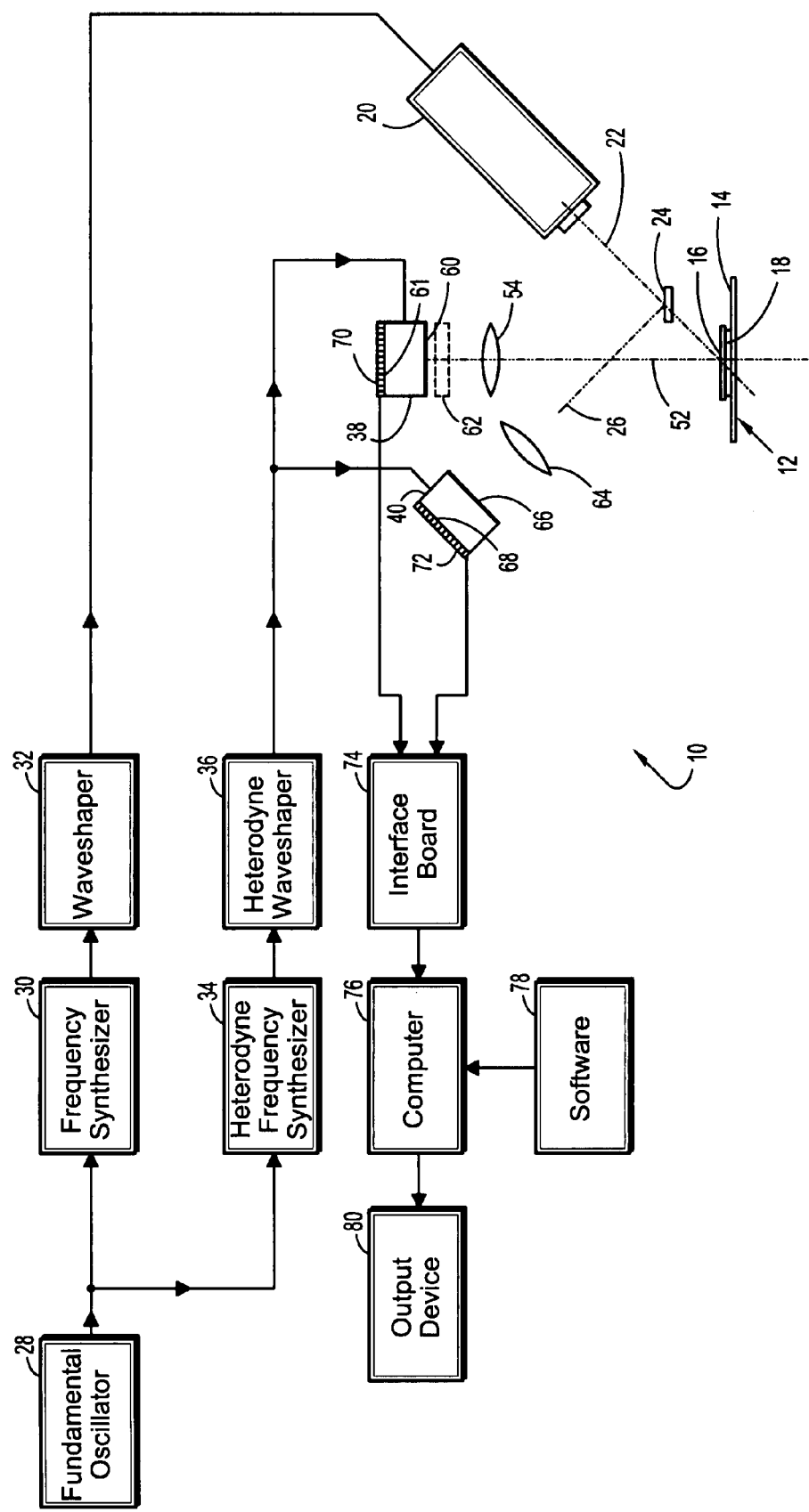
FIG. 1 is a block diagram of a system for implementing the method of the present invention.

Referring to FIG. 1, a fluorescence microscope system 10, illustrative of an example of an inventive luminescence image generating system, constructed in accordance with the present invention is illustrated. It is noted that the inventive system may be applied to fluorescence and phosphorescence systems and measurements. In particular, a slide 12 comprises a glass slide base 14 and a glass cover 16. Sample 18, which may be liquid, or a solid or dry material, is positioned between glass slide base 14 and glass cover 16.

Figure 2:
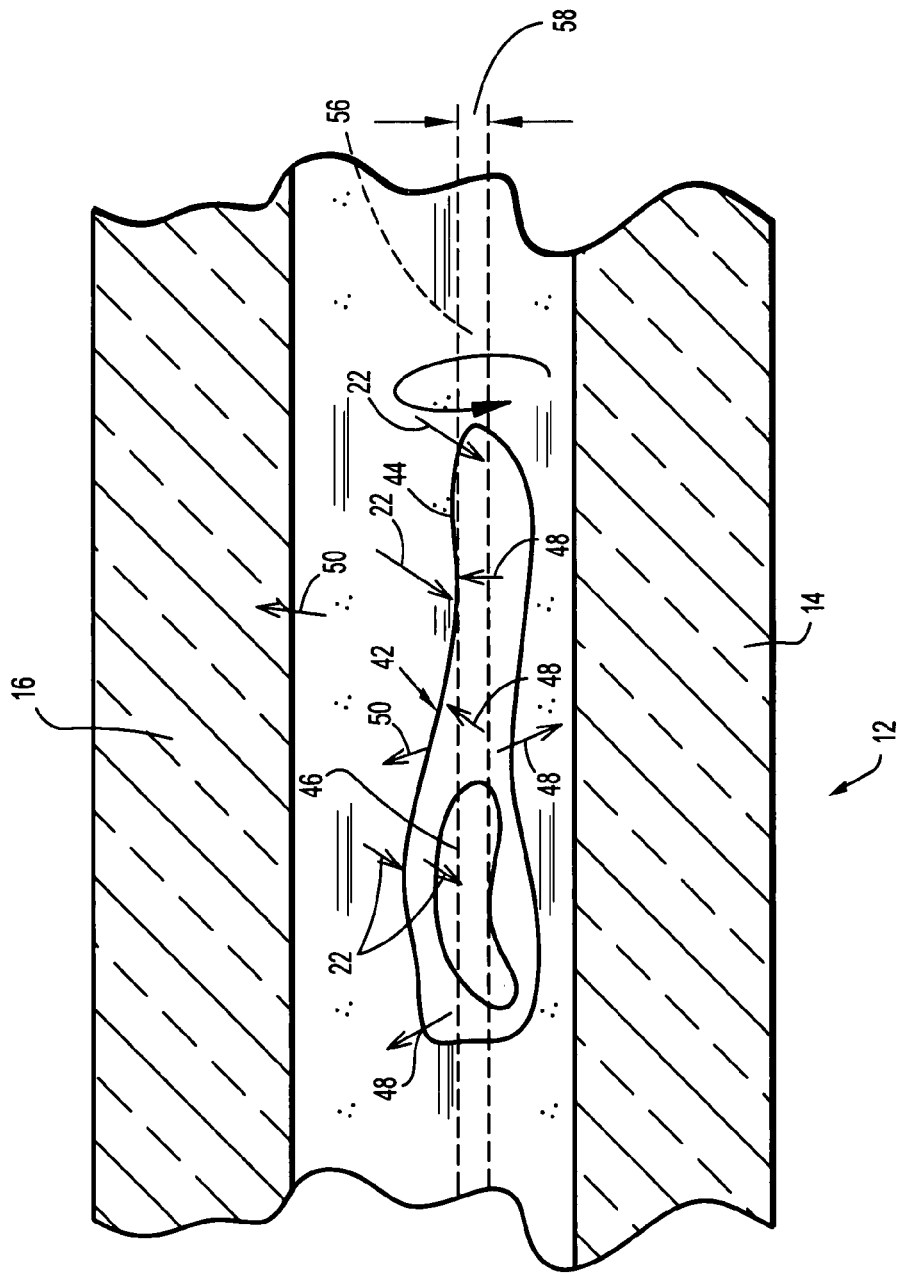
FIG. 2 is a detail showing a sample under observation by the inventive system.

Sample 18 is illuminated by a source of light such as laser 20, which outputs a pencil beam 22 of light which falls on sample 18 as illustrated in FIG. 2. Beam 22 passes through a partially-silvered mirror 24. Partially-silvered mirror 24 has the characteristic of reflecting only a very small portion of beam 22. In accordance with the preferred embodiment of the invention, partially-silvered mirror 24 reflects only as much of beam 22 as is necessary to generate a clear signal for use as a reference beam 26, as will be described below. Depending upon the nature of the reference signal detector optics and detector electronics, partially-silvered mirror 24 may reflect as little as two or three percent of beam 22. It is desirable to minimize the percentage of beam 22 which is diverted away from sample 18 to form reference beam 26, in order that the maximum amount of energy from beam 22 falls on sample 18 and, accordingly, the maximum amount of fluorescence radiation is produced for detection by the system.

It is noted that a partially-silvered mirror is an option for inclusion in the instrument. In many situations a partially silvered mirror is not used. It is to be understood that the inventive apparatus and method may be applied to other types of fluorescence systems.

As noted above, the inventive system relies upon a fluorescence signal stimulated by a modulated excitation light source. The same is achieved through the use of a fundamental oscillator 28 operating at the desired modulation frequency, typically in the range of 5 MHz. The output of fundamental oscillator 28 is sent to a frequency synthesizer 30 which generates a plurality of other frequencies. In accordance with one embodiment of the invention, frequency synthesizer 30 will output a signal at 5 MHz and at multiples of 5 MHz ranging as high as 300 MHz or higher. In accordance of the present invention, however, it is contemplated that the frequencies of signals output by frequency synthesizer 30 may have other values, as may be convenient and/or efficient to generate, and/or process as described below, provided that the desired range of modulation frequencies is covered with enough data points to perform a least squares curve fitting operation upon the data points within a desired statistical confidence interval.

In particular, in accordance with the invention, the method of least squares is used to fit a curve as close as possible to experimental data points produced by the system by minimizing the sum of the squares of the deviations of the experimental data points from the curve. In the case where the derivation of a curve describing the mathematical relationship between frequency and either modulation or phase, the functional type (linear, quadratic, exponential, sum of two exponentials, etc.,) is known, the method of least squares is used to determine the parameters of a general equation of that category.

Other statistical methods may also be used. In addition to estimating the parameters of the equation, the system may also be used to calculate standard error and a confidence interval. In addition, the inventive system 10 may be used even where there is no particular functional type that can be postulated as a starting point for the calculation. In such a case, standard fitting procedures may be used to gain insight into the subject matter under study. In addition, qualitative information respecting physical processes, for example as they vary over time, may be more easily understood after performance of a method of least squares approximation.

It is noted that a continuous wave source with either an intrinsic or external modulator, in accordance with this embodiment of the invention has a signal generator or synthesizer producing multiple coherent harmonics. Generally, a pulsed source only requires a fundamental frequency. The transform of a pulse is multiple coherent harmonics. In accordance with the invention, a pulsed source and a synthesizer controlling an array detector can be present in any system. Moreover, multiple synthesizer may be synchronized.

The shape and duration of the electrical pulses output by frequency synthesizer 30 may be adjusted by an optional waveshaper, which operates by conventional means. Such a waveshaper 32 may be driven by frequency synthesizer 30. In accordance with the invention, the output of frequency synthesizer 30 is adjusted to be the sum of electrical energy at the fundamental and other frequency synthesizer frequencies. The energy at the fundamental frequency may be understood as a first laser drive signal component. The energy at the next highest frequency may be understood as a second laser drive signal component. The electrical energy at the third highest frequency may be understood as a third laser drive signal component, and so on through the range of frequencies output by frequency synthesizer 30.

The output of synthesizer 30 is sent to laser 20 which emits laser energy with a desired optical wavelength, but modulated in intensity by the output of synthesizer 30, which constitutes a sum of the various frequency signals generated by frequency synthesizer 30.

A heterodyne frequency synthesizer 34 is synchronized to the output of fundamental oscillator 28 and outputs a plurality of heterodyne signals. There is a heterodyne signal associated with each of the output signals generated by frequency synthesizer 30. The frequency of each of these heterodyne signals is slightly different from the frequency of its associated laser drive signal. The construction of heterodyne frequency synthesizer 34 is conventional and similar to that of frequency synthesizer 30. Each modulation and heterodyn signal pair may preferably have a unique low frequency product. Thus, the difference in modulating frequencies is different for each associated laser drive signal and its respective heterodyne signal, allowing the digital filters to individually separate modulation products for each of the laser drive signals at their respective frequencies.

Thus, the first pair may comprise an output signal at 5 MHz and an associated heterodyne signal at 5.000005 MHz. The second pair may be 10 MHz and 10.000010 MHz, and so forth.

This difference may be, for example, 5 Hz for the first laser drive signal, 10 Hz for the second laser drive signal, 15 Hz for the third laser drive signal, and so forth. The various heterodyne frequency signals are then coupled to a heterodyne waveshaper 36 which forms output pulses having a desired shape, duration and delay.

In accordance of the preferred embodiment of the invention, the shape of the output from heterodyne waveshaper 36 comprises the sum of the various heterodyne frequency signals.

It is noted that, in accordance in the invention, a single frequency synthesizer may perform the combined function of frequency synthesizer 30 and heterodyne frequency synthesizer 34. Likewise a plurality of appropriate waveshaping circuits, each coupled to one of the outputs of the synthesizer circuits, may be used to synthesize the desired waveforms.

The output of the heterodyne waveshaper 36 is coupled to a sample image intensifier tube 38. The output of heterodyne waveshaper 36 is coupled to the reference intensifier tube 40.

As described above, light beam 22 illuminates a sample 18 which may include, for example, a cell 42. As illustrated in FIG. 2, cell 42 includes a membrane 44 and a nucleus 46. Cell 42 is contained in a liquid medium between slide base 14 and slide cover 16. When sample 18 is illuminated by light 22 from laser 20, the molecules comprising the cell are excited and fluoresce, emitting fluorescent radiation 48. Fluorescent radiation 48 is lower in energy than excitation source light 22, and, accordingly, it is of longer wavelength. In addition, a portion of light 22 may be reflected in various directions as light 50. Light 50, because it is simply reflected light, has the same wavelength as the excitation source light 22. A portion of both fluorescent radiation 48 and reflected excitation source light 50 travels along a path 52 (FIG. 1) toward microscope focusing optics 54, shown diagrammatically as a simple convex lens. In practice, microscope focusing optics 54 comprises a plurality of lenses in a confocal configuration, and including a number of masks to achieve the desired confocal characteristic. In particular, the desired confocal characteristic achieves focusing of objects in a narrow range of focus which consists of a planar volume 56 of relatively shallow depth 58, as illustrated in FIG. 2. The object of the use of the inventive fluorescence microscope system 10 is to view a cross-section of the object, such as cell 42 under view.

Microscope focusing optics 54 focuses both fluorescent radiation 48 and reflected excitation light 50 on the sensitive face 60 of image intensifier tube 38. During the normal operation of image intensifier tube 38, the optical image stimulates the formation of an electron image which is accelerated and triggers an avalanche to form an amplified image on the output face 61 of image intensifier tube 38. If desired, because of the relatively low level of fluorescent radiation 48 from a particular sample, reflected excitation light 50 may be blocked by a band-reject filter 62.

As discussed above, fluorescent radiation 48 has an amplitude and phase characteristic which varies from that of the excitation light 22 produced by laser 20. However, in order to measure this difference, a sample of the excitation light 22 reflected by partially-silvered mirror 24 as sample light 26 must be measured. Accordingly, sample light 26 is brought by focusing optics 64 onto the sensitive face 66 of an intensifier tube 40. The sample light 26 brought to sensitive face 66 is accelerated and amplified to form an image on the output face 68 of image intensifier tube 40.

It is necessary for the two amplified images on output faces 61 and 68 to be compared in order to determine modulation and phase information. This is done by providing output face 61 with a CCD detector 70, for example a 250 element by 250 element CCD or other suitable detector, preferably with a size and resolution matched to the output of image intensifier tube 38. The output of CCD 70 is thus an image of that portion of the sample focused by focusing optics 54 on sensitive face 60.

In similar fashion, output face 68 of image intensifier tube 40 is provided with a CCD detector 72, substantially identical to CCD 70. The output of CCD 72 is thus an image of that portion of the reference light traveling along path 26 and focused by focusing optics 64 on sensitive face 66 and serves as a reference with respect to which the sample image data may be compared to generate image information.

The outputs of image intensifier tubes 38 and 40 are sent to a computer interface board 74 plugged into a computer 76. Using conventional filtering techniques, interface board 74 and computer 76 (controlled by filter software 78) together separate out the amplitude and phase information for both the reference beam 26 and fluorescent radiation 48, and generate amplitude (modulation) and phase information for the fluorescent light emitted by sample 18. In addition, because this information is associated with two-dimensional spatial data in a given plane of focus, the fluorescence characteristic may be graphically shown on an output device 80 for visual or intuitive analysis and/or numerically processed with any desired criteria to achieve any desired quantitative output.

Before using the inventive system to perform a measurement on a sample, it is necessary to calibrate the system. This is done by first using, in place of a sample, a standard consisting of a zero lifetime scattering solution. When the instrument measures the zero lifetime scattering solution, it creates a set of normalizing phase and modulation standard values which function as a standard. These normalized phase and modulation values, obtained using the zero lifetime scattering solution standard, are compared to measured phase and modulation values created by the system when it measures the sample. The system generates the phase and modulation standard values in the same way in which it measures phase and modulation values for a sample, as will be described in detail below. The actual phase and modulation value for a particular point on the sample is the difference, respectively, between the phase and modulation values generated for the point on the sample and the phase and modulation value generated for the same point using the zero lifetime scattering solution standard.

During operation of the inventive system to measure the characteristics of a sample, laser 20 is excited to produce modulated laser light. A small portion of the modulated laser light is reflected by partially-silvered mirror 24. This reflected light takes the form of light 26 which is sent through optics 64 to sensitive face 66 of intensifier tube 40. CCD 72 then forms a reference modulated electrical signal. In the instant example of a 250 by 250 element image intensifier tube 40 driving a 250 by 250 element CCD 72, this reference modulated electrical signal takes the form of 62,500 individual reference signals, one corresponding to each element in CCD 72. All of these 62,500 individual signals each serve as a reference signal and are downloaded in a conventional manner and sent to computer 26 via interface board 74.

The bulk of the radiation produced by laser 20 passes through partially-silvered mirror 24 and falls on sample 18, causing it to fluoresce with an amplitude and phase different from the modulated (or pulsed) laser output of laser 20. Fluorescence emissions 48 from sample 18 then pass through optics 54 and are imaged on sensitive face 60 of image intensifier tube 38. Band reject filter 62 may have the characteristic of reflecting light at the output wavelength of laser 20. Accordingly, band reject filter 62 passes fluorescence emissions while blocking transmission of reflected light at the wavelength of laser 20 and preventing it from overloading image intensifier tube 38. Alternatively other filters, such as high pass filters, low pass filters or bandpass filters may be used, and, depending upon the particular measurement being performed, any one or more of these filters may provide a most nearly optimum characteristic for the detection of the fluorescence wavelengths of interest while at the same time minimizing the interference of noise in the inventive system.

Figure 3:
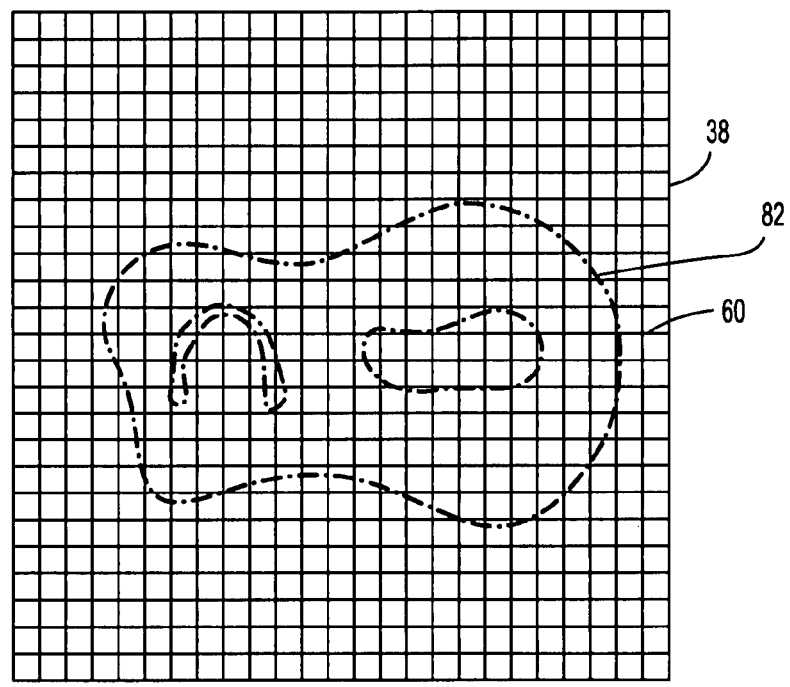
FIG. 3 illustrates a fluorescent image.
Figure 4:
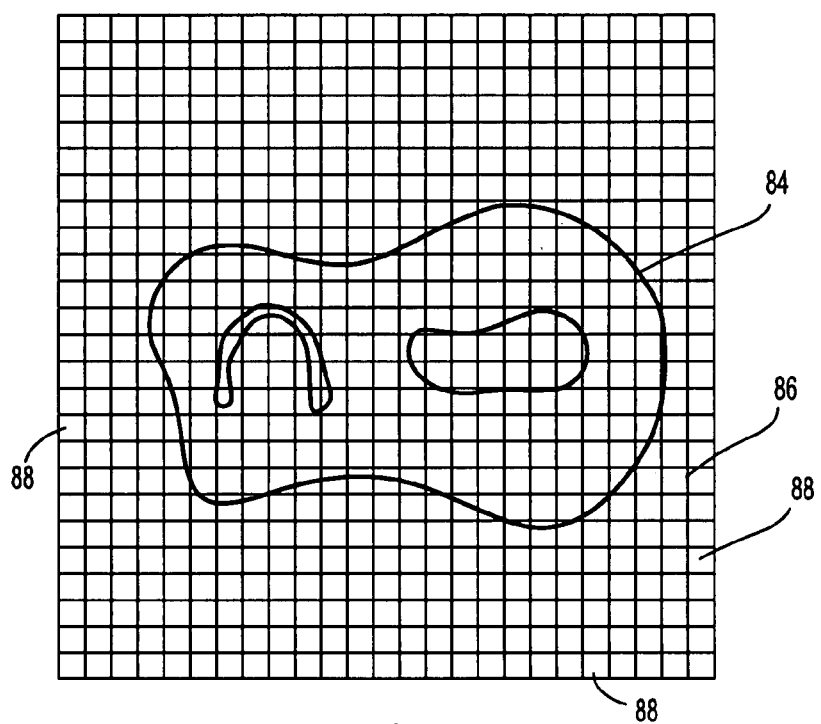
FIG. 4 illustrates an intensified fluorescence lifetime spatially resolved fluorescent image generated using the inventive method to gather spatial and multi-frequency data simultaneously.

This fluorescent light takes the form of fluorescent light 48, emitted by sample 18 when it fluoresces, and is focused as an image 82 (FIG. 3) by optics 54 onto sensitive face 60 of image intensifier tube 38. It is noted that in the figures, the illustrated number of elements of image intensifier tube 38 and CCD 70 is greatly reduced for purposes of clarity of illustration. Image 82 is accelerated and intensified by image intensifier tube 38 to form an intensified lifetime based fluorescence image 84, as illustrated in FIG. 4.

Intensified image 84 then falls on the front face 86 of CCD 70. CCD 70 then forms a measurement modulated electrical signal. In the instant example of a 250 by 250 element image intensifier tube 38 driving a 250 by 250 element CCD 70, this reference modulated electrical signal takes the form of 62,500 individual measurement signals, one corresponding to each element in CCD 70. Each of the 62,500 individual measurement signals is associated with one of the 62,500 individual reference signals output from CCD 72. These 62,500 individual signals each serve as a reference signal and are downloaded in a conventional manner and sent to computer 26 via an interface board 74.

In accordance with the preferred embodiment of the invention, each one of the 62,500 individual multifrequency measurement signals (for example, each containing a hundred single frequency signals, corresponding to a hundred excitation frequency modulation components associated with each pixel 88) is compared to its respective one of the 62,500 individual reference signals to generate phase and modulation information for the point on the image associated with the particular individual measurement signal and the point on sample 18 measured by the respective individual measurement signal. This is done by filtering the output of each pixel 88 to separate out the difference frequency modulation products (one hundred in the example of fifty modulation frequencies).

Figure 5:
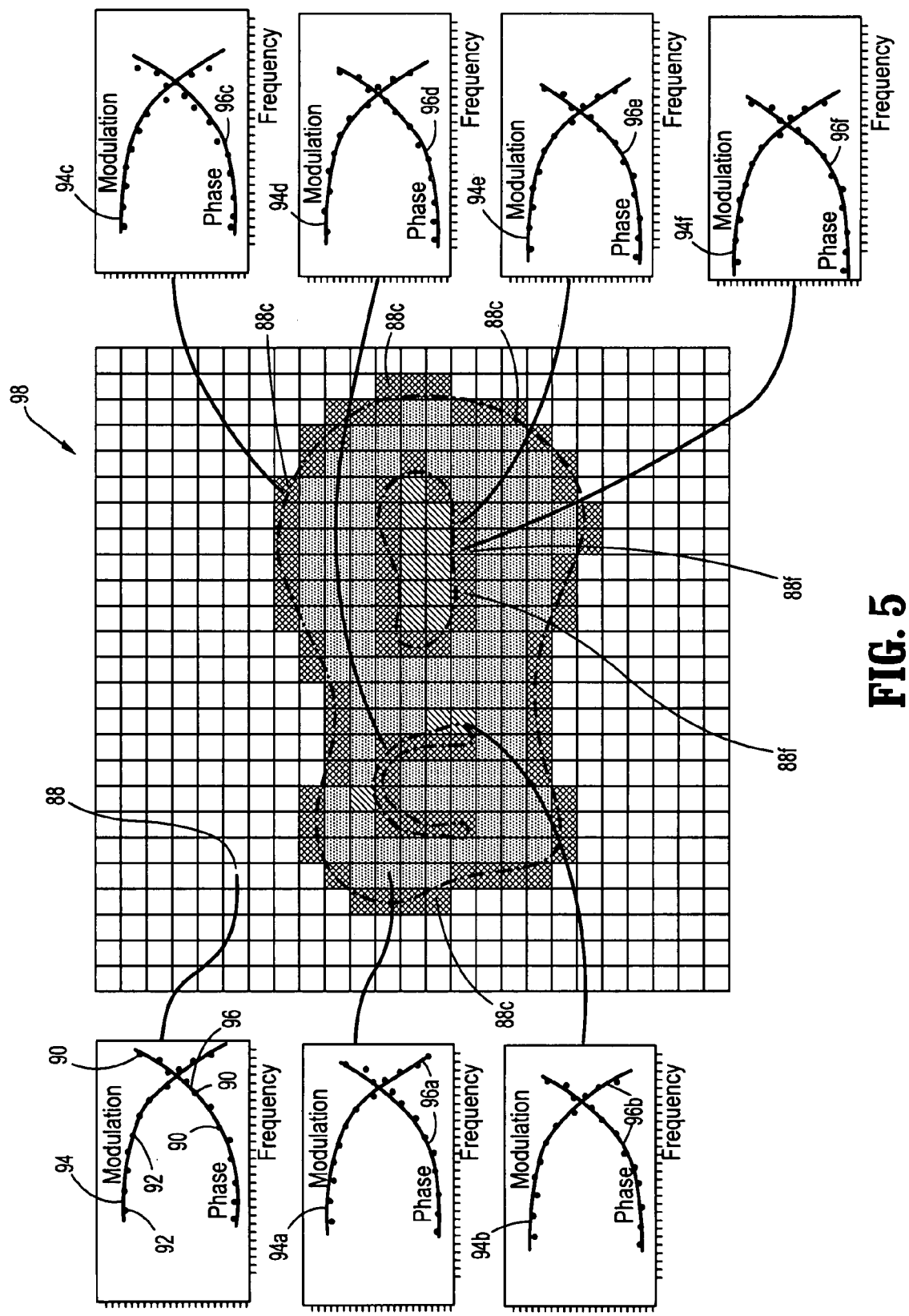
FIG. 5 illustrates an output from the inventive system together with various modulation and phase characteristics for pixels of an image which result in a particular value determination for fluorescence lifetime.

Thus, each pixel 88 generates a plurality of phase measurements 90, one for each of the excitation frequencies, as is illustrated in FIG. 5. In addition, each pixel 88 generates a plurality of modulation measurements 92 for these frequencies. This may be better understood when it is recognized that image intensifiers 38 and 40 act as mixers, mixing each of the heterodyne signals and its respective measurement signal.

Each one of the comparisons of respective measurement and reference signals for a particular point on sample 18 is performed individually for each of the modulation frequencies output by frequency synthesizer 30 to generate a pair of data points. In particular, there are modulation data points 92 (fifty for each pixel) and phase data points 90 (fifty for each pixel) for each of the fifty frequencies which is modulating the output of laser 20, as is illustrated in FIG. 5. Thus, as in the example above, if there are fifty different modulation frequencies used to modulate laser 20, each data measurement results in the generation of fifty modulation and fifty phase data points for each of the 62,500 individual measurement signals, or 6,250,000 data points for each interval of time over which a measurement is taken. Again, for purposes of illustration, the number of data points 90 and 92 illustrated in FIG. 5 has been reduced for purposes of clarity of illustration.

Generally, the duration of the interval over which the measurement is taken depends upon the intensity of the fluorescence information and the signal-to-noise ratio. Generally, as is known in the art, with high signal-to-noise ratios and fluorescent emission intensity, shorter intervals are sufficient to collect enough photons to achieve a good data point measurement.

Accordingly, intensified image 84 is turned into a plurality of modulation characteristic curves 94-94f and phase characteristic curves 96-96f. Each pixel receives a different excitation input and, accordingly, depending upon intensity and delay (that is modulation and phase), a plurality of modulation characteristics, for example, modulation characteristic curves 94, 94a, 94b, 94c, 94d, 94e, and 94f may be derived by computer 76. Likewise, a plurality of phase characteristics, for example, phase characteristic curves 96, 96a, 96b, 96c, 96d, 96e, and 96f, respectively, are also generated by computer 76. These phase and modulation characteristic curves correspond, respectively, to pixels 88, 88a, 88b, 88c, 88d, 88e, and 88f, and are illustrative of the calculations for the entire display.

For purposes of illustration, FIG. 5 is simplified to show a display 98 which shows calculation details for only a limited number of pixels and only seven different fluorescent lifetimes, with the shortest lifetime reflected by phase characteristic curve 96 and modulation characteristic curve 94. Characteristic curves 94a and 96a correspond to the next longest lifetime, of those illustrated. Characteristic curves 94b and 96b, 94c and 96c, 94d and 96d, 94e and 96e, and 94f and 96f, respectively, represent experimental data points for increasingly longer lifetimes.

If desired, display 98 may be color-coded or coded in shades of gray or otherwise, as illustrated in FIG. 5 to show different lifetimes with different graphical representations. These lifetimes may correspond to differences in physical characteristics. For example, in the image of cell 42, the cell wall tends to have a lifetime which may be derived from curves 94c and 96c and accordingly the display 98 includes a corresponding pixel 88c of identifiable characteristic appearance on display 98. Likewise, most of the edge of the nucleus is defined by pixels with the same measured lifetime as pixel 88f and is illustrated with a second characteristic appearance.

As may be understood from the above discussion, the inventive system results in a relatively high need for computing power. However, it is unnecessary that all of this computing power be concentrated in the general purpose, and thus more expensive, mainframe of computer 76, which may be a personal computer, or a more powerful system. In particular, the number of data points and the speed with which the same may be generated and processed for a given amount of computing power may be maximized by providing interface board 74 with storage and/or calculation functions in order to reduce the computational load on the accumulator of computer 76. The result is a significant increase in speed and/or data density.

Computer 76 then processes the measurement data points in a conventional manner, for example, using them to identify particular components and concentrations of those components.

While this system has been illustrated showing a cell, a semiconductor chip or other type of system may also be imaged and measured.

Figure 6:
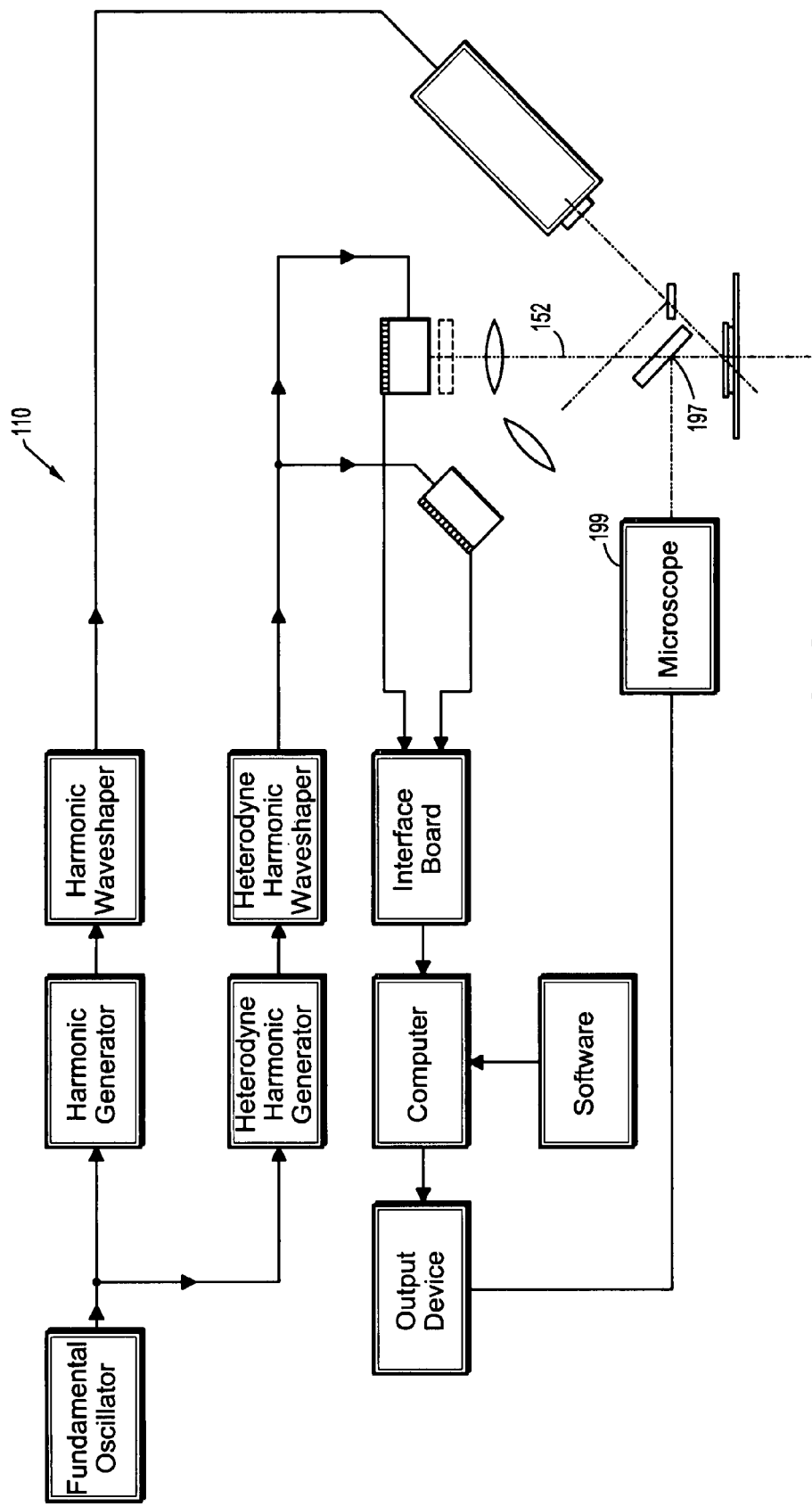
FIG. 6 is an alternative embodiment of a system for implementing the method of the present invention.

A second embodiment of the invention is illustrated in FIG. 6. In this embodiment, corresponding or analogous parts are numbered with numerals 100 higher than their corresponding parts in the FIG. 1 embodiment for purposes of succinct description in this specification. In particular, it is noted that the inventive system 110 illustrated in FIG. 6 is substantially identical to the system illustrated in FIG. 1, except for the introduction of a partially-silvered mirror 197 which reflects about 5 percent of the radiation to an optical microscope 199, which may be viewed by the human eye, used to make a photographic exposure, or any other desired output. This is of particular value if a relatively low power computer is used, or a great number of data points are being acquired, as real-time adjustment of the system can be done initially using microscope 199. Alternatively, it is noted that partially-silvered mirror 197 may be made completely reflective, provided that it is provided with a mounting which slides it into optical path 152, when it is being used, and removes it completely from path 152, when its use is not needed.

Figure 7:
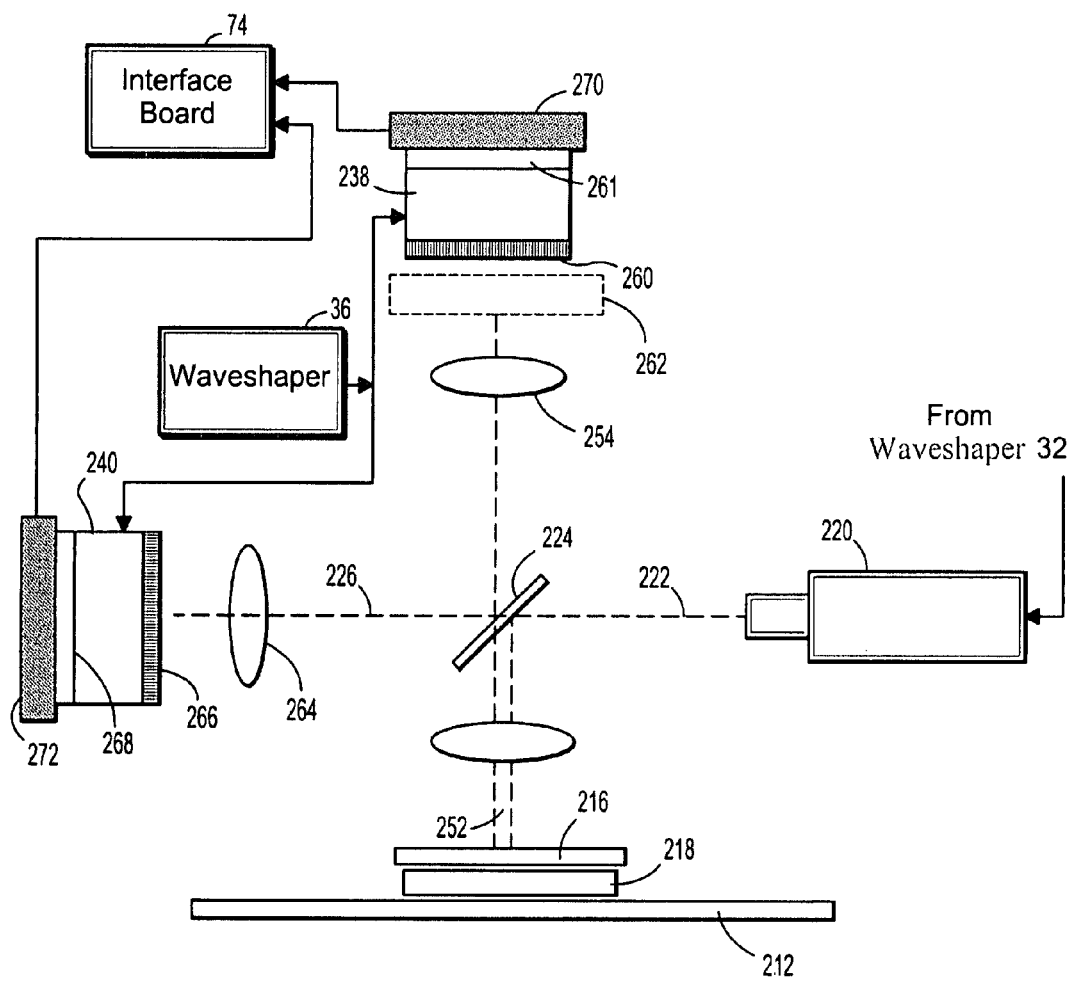
FIG. 7 is an alternative embodiment of an optical arrangement useful in, for example, the systems for implementing the method of the present invention illustrated in FIGS. 1 and 6.

A particularly advantageous optical arrangement for an optical system to be employed, for example in either the system of FIG. 1 or the system of FIG. 6, is illustrated in FIG. 7. In this embodiment, system elements corresponding to the elements of FIG. 1 are numbered 200 and higher and perform substantially the same function, except that light from source 220 is reflected by partially-silvered mirror 224 onto sample 218, and fluorescence radiation is passed by mirror 224 to collection optics 254 and the detector which it images. This arrangement has the advantage of maximizing the fluorescence signal compared to other light in the system, on account of the angular relationship between the optical members, excitation source and sample.

The above-described system has substantial advantages in its presentation of fluorescence data as a function of position of an entity, such as a biological entity, being studied.

For the sake of convenience, such information may be described as an image, but it should be understood that the invention, contemplates the processing of the data by computer and the presentation of mapped data as visual images which may or may not simulate an optical or theoretical optical examination of the entity. It may even be displayed as an image. For example, an entity may be represented schematically as a sphere or oval, with a particular structure or composition diagrammatically indicated as, for example, a plus sign. Likewise, a structure may be illustrated as a simplified shape with the area penetrated by agent marked with dots. Alternatively, the information, for example fluorescence information or phosphorescence information mapped to location may be processed without ever being imaged either conceptually or using a display.

In the context of the above-described system, performance may be optimized by tailoring excitation frequencies, amplitudes and implementations to improve system signal-to-noise ratio and, accordingly, system speed.

A first step which may be taken in this direction is to generate all excitation frequencies through the use of a master oscillator. This has the result of synchronizing (but not aligning) the phase of all excitation frequencies. Accordingly, errors in the determination of phase and magnitude are avoided, but the use of non-harmonic and/or incoherent sources allows achievement of high average power excitation light sources.

Improved signal-to-noise ratio may be obtained by improving the depth of modulation. While 100% depth of modulation is desirable, the prior art technique of applying a modulation signal to the dynode of a photomultiplier tube achieves only approximately 10 to 20% depth of modulation. In accordance with a preferred embodiment of the invention, 100% depth of modulation is achieved through the use of a Pockel's cell.

In the prior art, both Mitchell and Gratton (U.S. Pat. No. 5,257,202), disclosed techniques for parallel phase flourem-etry. Both used the concept of pulses generating coherent harmonics. Gratton used a variable pulse width generator, Mitchell an SRD diode. Both had the goals of speeding up the measurement to reduce data collection times.

In a typical prior art multi-harmonic Fourier fluorometer, such as that illustrated in U.S. Pat. No. 4,937,457 of Mitchell, the harmonics produced are coherent (synchronized and aligned(in phase) with each other. It is noted that the Fourier transform of a pulse in the time domain is an infinite number of harmonics in the frequency domain In a typical system of this type, a plurality of harmonic signals, equispaced in the frequency domain, result in the time domain in relatively short high power pulses separated by relatively is long periods of relatively low power signal strength. Thus, the root mean square amplitude of the signal stimulating fluorescent emission is relatively low. Accordingly, superior signal-to-noise ratios cannot be achieved. In addition, the design of an amplifier for signals with low root mean square values and high peak values is not an efficient use of amplifier dynamic range and tends to increase amplifier distortion products and costs.

In accordance with one aspect of the invention, peak power is reduced, average power maximized by selecting incoherent (out of phase) harmonics and/or logarithmically spaced frequencies. However, a master oscillator is used in order to maintain any desired phase relationship between the components. Because this relationship is known, such information is used by the system to minimize errors in the measurements produced by the system. Frequencies which maximize the differences one wishes to detect may also be used.

The inventive system thus utilizes lower peak powers and higher root mean square energy, and achieves superior signal-to-noise ratios. Moreover, in accordance with the present invention, all signals are run off a master oscillator, thus minimizing the need for calibrations and reducing errors in the determination of phase and magnitude.

It is noted that the definition of a harmonic is a wave whose frequency is a whole-number multiple of the frequency of another. Thus, the fundamental frequency may be referred to as the first harmonic. It is noted that the term "coherent" refers to harmonic signals which are all in phase with each other. Harmonic signals which are out of phase with each other, even by known and fixed amounts, are referred to as "incoherent". Such signals, in accordance with the present invention, which are out of phase with each other by known and fixed amounts have the advantage of being able to be designed to have high RMS power values while minimizing peak-signal values, The use of logarithmically spaced frequencies (by definition they have no phase relationship) is even more efficient for maximizing average power while minimizing peak power.

Because many systems in the natural world have logarithmically based responses, in accordance with the invention, logarithmically spaced harmonics may be used to observe such systems, while improving the use of amplifier gain, reducing peak powers and improving signal-to-noise ratio. The inventive approach also contemplates not wasting power on harmonics which are not likely to convey information.

As the term "incoherent" is used in this application, it refers to signals which are not in phase. In accordance with the invention, the degree to which a signal is incoherent and out of phase with other signals may be adjusted to result in a high root mean square signal value and attendant high signal-to-noise ratio.

The use of logarithmic frequencies for source and detector modulation has the desirable fact of minimizing distortion products. This is the case because distortion products are always harmonics of the fundamental frequencies. Since logarithmic frequencies are never integer multiples of the fundamental frequency any distortion will not ultimately affect the cross correlation product.

For example, for a first Fundamental at 10 MHz, distortion is at 20 MHz, 30 MHz . . . etc. For the second Fundamental at 20 MHz, distortion is 30 MHz, 40 MHz, . . . etc. Note the overlap between the distortion at 10 MHz (20 MHz) and the fundamental at 20 MHz.

For a logarithmic system with 16 frequencies, consider a start frequency of 1 MHz, and an end frequency of 320 Mhz, i.e. 1.0, 1.5, 2.2, 3.2, 4.7, . . . 320. For the first Fundamental at 1 Mhz, distortion is at 2 MHz, 3 MHz . . . etc. For the second Fundamental at 1.5 MHz, distortion is at 3.0 MHz, 4.5 MHz, . . . etc. Note that there is no overlap between any fundamentals or distortion products.

To better understand the inventive system, it should be kept in mind that phase fluorometry uses two types of frequencies. Modulation frequencies on the light source and detector and the addition of cross-correlation/hetrodyne frequencies for the down converting/mixing of the modulation frequencies. Modulation frequencies are usually between 500 Hz-320 MHz. Cross-correlation/hetrodyne frequencies are 4 Hz-40,000 Hz. The mixing of the modulation frequencies produces a signal composed of the sum, difference, and modulation frequencies. Each frequency contains the amplitude and phase information. In accordance with the invention, everything is filtered out except the difference frequencies. The difference frequencies are low enough in frequency that they can be digitized.

In accordance with another preferred embodiment of the invention the modulation frequencies can be generated through the use of independently programmable synthesizers which will output a desired frequency, phase and amplitude in the range between 1 kHz and 320 MHz. In accordance with the invention, it is contemplated that as many as two sets of 24 synthesizers each would be employed. One set of the 24 synthesizers is for modulation of the light source. The other set is for modulating the detector, and have frequencies slightly offset from the frequency of the corresponding excitation modulation. The advantage of synchronizing all of the oscillators is that the phase relationship can be fixed in order to minimize the peak power and maximize the average power.

In accordance with another preferred embodiment of the invention, the waveforms which are used as an excitation source or a heterodyne signal may be generated in a number of ways. For example, individual components may be generated and summed. A dedicated frequency generator may be used as an input.

Alternatively, in principle, the signals may be generated by the computer being used to analyze fluorescence data. Of course, this requires sufficient computing power, and may be facilitated by an appropriate interface board.

One possible embodiment takes the form of using a computer to generate the excitation source and heterodyne signal waveforms, which would be composed of 1-24 or more incoherent harmonic or logarithmic frequencies. These may be fed in real time to a digital to analog converter.

Another embodiment of the inventive method comprises calculating the sum of a plurality of incoherent harmonic waveforms, loading such waveform sum into the memory of a computer and then repeatedly outputting values corresponding to the waveform stored in memory into a digital to analog converter for output as an excitation source or, heterodyne signal waveform. In connection with this, it is noted that harmonics are periodic, while logarithmic frequencies are not periodic.

Alternatively, the system may be programmed to follow a preset routine to randomly test the effectiveness of a wide range of waveforms, and using information gained along the way to limit further testing and direct further testing of true harmonic or other content likely to yield high signal-to-noise ratios and examined-object feature differentiation.

The desired modulation signal for the fluorescence excitation source may be implemented with a variety of hardware. For example, the signal may be implemented in the digital domain using an integrated circuit synthesizer and/or applying frequency doubling, frequency combining (adding frequencies) and so forth.

Also in accordance with the invention, a resultant repetitive waveform resulting from the addition of a plurality of harmonics, of the excitation modulation frequencies for the light source determined in accordance with any of the above techniques, may be calculated and synthesized and replayed from random access memory within which it is stored.

For example, a pulsed dye laser, or a continuous wave laser whose output is externally modulated by a Pockels cell or an LED which is intrinsically modulated may be employed in accordance with the present invention. However, it is becoming increasingly true that almost any light source can be either modulated or pulsed. In accordance with the invention, it is contemplated that the source used for exciting the molecule or material under study may be any one of numerous sources used in fluorescence emission studies. For example, a laser, such as a ruby or argon ion laser or a solid state laser, may be used, or a more conventional source, such as a metal arc (such as a mercury vapor or), metal halide or xenon arc lamp. As alluded to above, modulation may be implemented by passing the excitation source to an intensity modulating device such as a Pockels cell or or a Mach-Zender modulator.

There are several ways to modulate a detector. Modulation may occur before the detector using a micro channel plate for CCD detectors. Modulation may be performed within photomultiplier tube. Similarly, the fluorescence emission may be demodulated by application of a signal to a detector, such as a photomultiplier tube, or the fluorescence emission may be modulated a second time to create the desired low frequency heterodyne using a Pockels cell, or a Mach-Zender modulator. Still yet another alternative is to send the electrical output of a detector, such as a photomultiplier tube, to an electronic mixer for demodulation.

Likewise, the optical signal which is being modulated may be from a single source of a single wavelength, or it may be a source with multiple wavelengths.

In accordance with the present invention, the gathering of data and associated processing of a large number of data points for a plurality of pixels in the image of an object represents a substantial computing task. The efficient completion of this task can maximize the amount of information which may be gathered, while, at the same time, maximizing the signal-to-noise ratio of collected data and, accordingly, its reliability, speed and precision.

In principle, a fast Fourier transform is a good general purpose tool, particularly when one does not know the frequencies of interest. However, it suffers from the necessity of requirement of having $2^n$ samples. This corresponds to a requirement for $2*N*\log_2(N)$ calculations. These calculations require a large block of computing time or very significant computing power. When N (which must be integer) becomes large each increment can require a large amount of time.

Alternatively, a discrete Fourier transform may also be employed. Because the discrete Fourier transform is more focused, because it is based upon a knowledge of the frequencies of interest, this allows experimental runs which are not comprised of $2^n$ samples. Accordingly, computing time is reduced with concomitant reductions in the need for computing power, requiring only $2*N*$number of frequencies calculations.

The chirp z transform represents a significant improvement over the use of a discrete Fourier transform, as it decouples the input and output points, allowing any number of inputs and an arbitrary number of outputs.

However, the chirp z requires integer spacing between modulation frequencies, although it does permit any frequency to be chosen as the start frequency (in the set of modulating or excitation frequencies).

In accordance with the inventive adjunct to the chirp z transform developed in accordance with the present invention, sample rates may be dramatically reduced, thus simplifying the selection of integer spacing needed to satisfy the chirp z requirements.

When it is desired to use one of the inventive methods described above, the first step is to select the desired time resolution. This is done by determining whether the investigation is interested in a steady state measurement (where a relatively slow collection of data may be conducted) or a situation where there is a physical change (such as a chemical reaction or biological phenomena) taking place during the course of the experiment and we want to monitor that change over time as it occurs. This second situation where the physical change is occurring is known as a kinetic reaction and usually refers to the physical changes accompanying the performing of a chemical reaction. As compared to steady state measurement, kinetic reactions generally require much quicker data collection and, correspondingly, much smaller time resolution.

In the first case, that is the steady state measurement situation, we have a static sample which is being excited, for example, with a particular wavelength of light modulated at a particular frequency, for the purpose of analyzing the content of the material. This is not likely to be a time-critical measurement and gives the researcher substantial leeway in terms of the sampling time, time resolution and so forth.

More demanding is the case of a kinetic reaction. Design of an experiment may start with the length of time which the reaction takes to the perform. For example, the reaction may take one second to perform and the researcher may want a picture of the state of the reaction every 10 milliseconds. In this case, the time resolution would be 10 milliseconds. However, for each resolved temporal point in the experiment, it is necessary to take numerous data points, as is detailed above and appears more fully below.

One must also select the wavelength of light which will be used to cause the sample to fluorescence. The selection of the excitation wavelength generally determines which excitation light source will be used to stimulate a fluorescent emission. In connection with this, it is noted that the principles discussed here, and the instrumentation involved, also apply to other types of emissions where the excitation energy may be modulated, including, for example, other types of optical excitation, such as such systems utilizing Raman emission spectroscopy. The particular wavelength to be used to study a particular reaction may be known, or it may be experimentally determined by trial and error. Likewise, other factors, as is typical in research into the unknown, may be adjusted or even radically changed as information is gathered from the first experiments, or information from different experiments points to experimental parameters for future information gathering. In this respect, the use of the inventive methods for scientific investigation may be employed in conjunction with the experimental approach generally used in scientific investigation.

Once the wavelength of the excitation light has been determined, the next step is to determine the wavelength of emitted light. This identifies the detector to be used, together with any filters or other devices which may be used as would be employed in investigations and experiments conducted using existing fluorometric instrumentation.

For example, consider a situation where the kinetic reaction is expected to have a duration which is consistent with a time resolution of one millisecond. In other words, it is believed that useful data can be collected relating to the kinetic reaction if one looks at what is going on once every millisecond. This information may be observed for numbers of milliseconds, numbers of seconds, or longer depending upon the information learned during the experiment or earlier runs of the experiment. This period of one millisecond is referred to as the time resolution (TR) of the experiment.

The investigator must also determine the number of modulation frequencies to be used during the experiment. More particularly, it must be kept in mind that the phase and amplitude of fluorescence energy emitted in response to the excitation wavelength will provide the desired information. Typically, modulation frequencies in a range having an upper limit and lower limits separated by two orders of magnitude, for example 10 kilohertz and 1000 kilohertz are selected.

The next point is to determine the spacing of the modulation frequencies. For example, the modulation frequencies may be 10 kilohertz, 20 kilohertz, 30 kilohertz, 40 kilohertz, etc. to the 1000 kilohertz upper limit. Alternatively, in accordance with the above teachings of the present invention, the spacing may be logarithmic to satisfy other criteria (or approximately logarithmic in order to satisfy other requirements of the present invention), more particularly specialized conditions or carrying out the Chirp Z transform, as appears more fully below.

In accordance with the invention, the spacing may be integer spacing, provided that the chirp z and other criteria are used to select those frequencies.

Looking at the first signal, that is the 10 kilohertz modulation frequency, this signal is used to modulate the excitation light source. However, the sample emission in response to the 10 kilohertz modulation must be mixed with another hetrodyne signal to obtain a cross-correlation product. This, for example, is analogous to the signal applied to one of the plates on a photomultiplier tube in a prior art system. Alternatively, the signal and the heterodyne signal may be sent to a mixer.

One uses the following criteria to select the cross-correlation product. In the instant example, a time resolution of one millisecond is selected, and the excitation frequency is 10 kilohertz, the heterodyne frequency may be selected to be 14 kilohertz, giving a cross-correlation product of four kilohertz. The four kilohertz difference is needed in order to obtain four sine waves (and thus a reasonable signal-to-noise ratio) of the four kilohertz cross-correlation product within the desired one millisecond sample time. As a matter of instrument design, the heterodyne frequency is likely to be set in the instrument, by being determined internally by a subroutine in the instrument software.

In accordance with the present invention, it has been discovered that if the lower frequency in the range of excitation modulation frequencies, in the instant example 10 kilohertz, is linked to the difference between successive modulation frequencies (in the range between 10 kilohertz and the upper limit of 1000 kilohertz, mathematical processing in accordance with the Chirp Z transform is simplified by selecting the difference $\Delta f$ between a particular modulation frequency and the heterodyne frequency. Thus, the selection of the heterodyne frequency is a function of the number of sine waves needed to obtain a good reading within the period associated with the desired time resolution, for example, three or four sine waves, and the frequency of the primary modulation frequency (these two factors thus setting a minimum hetreodyne frequency), and a precise value determined by the inventive implementation of the Chirp Z transform process.

In accordance with prior art systems, once the fundamental frequency for modulation had been selected and the heterodyne frequency determined, other modulation frequencies in the range were multiples of the fundamental frequency and other heterodyne frequencies in the range were multiples of the sum of the fundamental frequency (which may also be referred to as the first harmonic) and the selected hetrodyne frequency associated when the fundamental frequency.

In contrast, in accordance with the invention, the next frequency for modulating a light source exciting the sample may be 20 kilohertz (or some other frequency selected in accordance with the above teachings). However, the hetrodyne frequency would not necessarily be 28 kilohertz. Rather, it would be selected to be 20 kilohertz plus a $\Delta f$ in accordance with the methodology of the invention to have a value which simplifies the calculation of the already relatively simple Chirp Z transform.

More particularly, in accordance with the invention, it has been discovered that if the $\Delta f$ is selected to be equal to the cross-correlation product $f_0$ (in the instant example 14,000 kilohertz minus 10,000 kilohertz) divided by $2^m$, i.e. $\Delta f = f_0 / 2^m$ (where m is an integer), calculation of the chirp z transform is greatly simplified. In the present example, m has been set equal to 2.

As an aside, if m were set equal to zero, it would be the conventional Chirp z transform calculation. In the instant example, we have set m equal to two. This is arbitrary. However, if we set m equal to, for example, four, the following consequences would ensue. Because two to the fourth power is equal to sixteen, taking the cross-correlation frequency $f_0$=4000 kilohertz, 4000 divided by 16 equals 125. Thus, $\Delta f$ is 125 hertz and $f_{max}$ becomes 3750 hertz out of the requirement for integer spacing with the Chirp z transform, expressed by the equation: $f_{max} = f_0 + (N-1) \Delta f$. Thus, because $f_{max}$ is lower with m=4 there will be fewer samples any given time period as compared to setting m=2. However, this may not be enough samples to satisfy the objectives of the experiment.

Returning to the illustrated example where m=2, the decision has been made to use 16 as the number of modulation frequencies N. N is set equal to 16 frequencies because experience has proven that this provides an acceptable statistical fit in typical fluorescence spectroscopy situations.

In accordance with the invention, $$\Delta f = f_0 \cdot 2^m,$$

where (m=0, 1, 2, . . . ). In the instant example, m=2, and $f_0$=4000 Hz. Given the above parameters, $\Delta f$ is equal to 1000 hertz. Thus, we can define the time resolution $T_r$ as:

$$T_r = 1/\Delta f, \text{ or}$$

in the present example, $$T_r = 1 \text{ millisecond}$$

We can calculate $f_{max}$, using the equation:

$$f_{max} = f_0 + (N-1)\Delta f.$$

Given the above parameters, we find $f_{max}$ equal to 19 kilohertz. The number of data points k will determine the quality of the reading. However, the more data points collected, the longer it takes to do the calculation. In the instant example, we have set k=32 samples per sine wave.

In accordance with one aspect of the invention, it is desirable to create a relationship between $f_0$ and $\Delta f$ to maintain the requirement of the inventive variation of the chirp z that K be an integer, where K is defined by the equation:

$$K = k(f_{max}/f_0) \cdot 2^m$$

Applying the inventive chirp z conditions, we calculate K=608.

Given these parameters, the system modulates the output light source with 16 different modulating frequencies, each of which has its own cross-correlation frequency. Each heterodyne frequency is the sum of the respective modulating frequency and the cross-correlation frequency, F(n), defined by the expression:

$$F(n) = f_0 + (n-1)\Delta f,$$

where n is the number of the modulating signal in the sequence of increasing frequency for the set of N modulating frequencies, and $f_0$ is the cross-correlation frequency for the first, lowest frequency, modulating signal (n=1).

As noted above, a plurality of modulating frequencies are applied to the light source which is exciting the sample. Accordingly, if the lowest modulation frequency is 10 kilohertz (n=1), and the next highest modulation frequency selected on the basis of, for example, a logarithmic, or approximately logarithmic, system is 30 kilohertz (n=2), the cross-correlation frequency F(2), for the 30 kilohertz modulating frequency, is equal to F(2)=4 kilohertz+(2−1)1000 hz=5 kilohertz Thus, the second hetrodyne frequency is 35 kilohertz which mixes with the 30 kilohertz second modulating frequency to generate a five kilohertz cross-correlation frequency signal to be used by the instrumentation.

The above process is repeated for each of the remaining 14 modulation frequencies, of the total of sixteen modulating frequencies.

Using this process, the modulating frequencies and their associated hetrodyne frequencies are identified. The modulating frequencies are summed to modulate the excitation laser. This excites the sample under observation, such as biological entity, causing the generation of an output fluorescence. The fluorescence signal is imaged into a plurality of pixels, each of which has a time varying electrical output having amplitude, frequency and phase components. As discussed above, each point on the object under observation emits light which is imaged by an associated light contacting pixel. This results in generating the time varying electrical output having amplitude, frequency and phase components, as discussed above. This time varying electrical output having amplitude, frequency and phase components may be periodically sampled by using an analog-to-digital converter to sample the waveform, in the instant example, every 10 milliseconds. Each sample is the integration of its respective signal over a time period equal to the duration of, for example, four sine waves of the cross correlation (mixer output) signal. The duration of the four sine waves of the mixer output signal is less than the 10 milliseconds between samples, but additional samples would increase the amount of data that needs to be processed mathematically and thus such data is not taken.

Thus, for the composite modulating signal comprising the sum of the sixteen modulating frequencies, we take a set of signal samples (32 samples per sine wave or 128 samples) corresponding to the duration (128/4000 seconds or 32 milliseconds) of four sine waves of the cross-correlation signal associated with the lowest frequency modulation frequency modulating the excitation laser. These 128 samples define the waveform of the emitted fluorescence signal. When compared to the excitation signal, using the hardware described above, frequency, amplitude and phase (delay) information is obtained.

In the instant example one employs the chirp z transform, $$H(n) = \sum_{K=0}^{K-1} \times (k) e^{-j2\pi k f_0/S_r} e^{-j2\pi k(n-1)\Delta f/S_r}$$

where H(n) is a complex number representing the amplitude and phase of one frequency component of the detected fluorescence signal, K is the length of the chirp z transform in data points (in the example 128 data points per pixel per millisecond spread over four sine waves of the mixer output cross-correlation signal), and N is the total number of modulation frequencies, and n is the frequency index or the number of the particular modulating frequency in the set of ascending modulating frequencies.

In accordance with the specialized adjunct conditions associated with the present invention, the calculation is associated with the chirp z transform are simplified.

Thus, the signal, for each pixel of an image of an object or space under observation is sampled every 10 milliseconds, with each 10 millisecond sample corresponding to, in the example, four sine waves (at 32 samples per sine wave) or K=128 data points. Each of these sets of 128 data points is analyzed using the chirp z transform, and the amplitude, frequency, and phase information compared to standard data, generated using known samples, to determine the characteristics of each point on an imaged subject.

It will be appreciated from the foregoing that the efficiencies provided by the inventive adjunct to the chirp z are of particular value. In particular, it is noted that in an imaged array, for example, of 20,000 points every 10 milliseconds, it is necessary to digitize 128 samples, for total of 2,640,000 samples and this corresponds to a very large number of calculations.

While illustrative embodiments of the invention have been described, it is understood that various modifications may be obvious to those of ordinary skill in the art. Such modifications are within the spirit and scope of the invention, which is limited and defined only by the appended claims.

The invention claimed is:

1. A method of spectrographic measurement, comprising:
   (a) generating a plurality of modulation signals at a plurality of modulation frequencies;
   (b) coupling said modulation signals to an excitation source, said excitation source producing excitation light for illuminating a sample to be assayed, to vary the amplitude of said excitation light by modulating said excitation light with said plurality of modulation signals;
   (c) sampling a portion of said excitation light which has been varied in amplitude to form a reference optical excitation signal;
   (d) illuminating said sample to be assayed with said excitation light, causing said sample to emit an output optical signal;
   (e) imaging said output optical signal on a multielement optical detector having a plurality of elements, whereby each of said elements is associated with a region on said sample to be assayed;
   (f) generating a plurality of measurement signals using said multielement optical detector, each measurement signal associated with a single one of said elements;
   (g) generating a plurality of heterodyne signals at a plurality of heterodyne frequencies, each of said heterodyne frequencies being associated with one of said modulation frequencies;
   (h) for each measurement signal associated with an element of said multielement optical detector, mixing said measurement signal with said heterodyne signals to generate a plurality of low-frequency measurement modulation products, one low-frequency measurement modulation product being associated with each of said modulation frequencies and comprising the difference between a respective modulation frequency and its associated heterodyne frequency and having a measurement amplitude and phase;

(i) mixing said reference optical excitation signal with said heterodyne signals to generate a plurality of reference modulation products, one reference modulation product being associated with each of said modulation frequencies and comprising the difference between a single modulation frequency and its associated heterodyne frequency and having a reference amplitude and phase, each of said reference modulation products being associated with one of said low-frequency measurement modulation products; and (j) for each of said plurality of low-frequency measurement modulation products, comparing said low-frequency measurement modulation product to its associated reference modulation product to generate an output signal indicating characteristics of said sample at the region on said sample associated with each of said elements.

2. The method of claim 1, wherein said modulation and heterodyne signals are logarithmically related.

3. The method of claim 1, wherein said modulation signals are incoherent.

4. The method of claim 1, wherein said modulation signals are out of phase with each other.

5. The method of claim 1, wherein said excitation light is generated with a laser.

6. The method of claim 1, wherein said output optical signal comprises fluorescent energy from said sample.

7. The method as in claim 1, wherein said modulation frequencies are selected to have a high root mean square value.

8. The method as in claim 1, wherein said excitation source is a laser and wherein the excitation light is modulated by a Pockel's cell.

9. The method as in claim 1, wherein said excitation source is a laser whose output is a pulsed laser output.

10. The method of claim 9, wherein said laser is a pulsed-dye laser.

11. The method as in claim 1, wherein said excitation source is a light emitting diode or other solid-state laser device.

12. The method of claim 1, wherein said reference modulation products are the low-frequency reference modulation products output during said modulation.

13. The method as in claim 1, wherein said comparison is done by measuring the relative phase and amplitude of said low-frequency measurement modulation product as compared to said reference modulation product and generating a modulation data point and a phase data point.

14. The method as in claim 13, further comprising:
(a) for each element, fitting said modulation data points to a first curve using the method of least squares;
(b) for each element fitting said phase data points to a second curve using the method of least squares;
(c) comparing said first and second curves to a database to determine characteristics of said sample; and
(d) displaying said characteristics.

15. The method of claim 1, wherein before said excitation energy output by said excitation source is caused to fall on said sample to be measured, a system is calibrated by first using, in place of said sample, a standard consisting of a zero lifetime scattering solution to create a set of normalizing s phase and modulation standard values against which said phase and modulation values for said sample are measured.

16. A method as in claim 1, wherein said modulation frequencies are selected for known sensitivity to a parameter being measured.

17. A method as in claim 1, wherein frequencies are selected to simplify use of a chirp Z transform.

18. A method as in claim 1, wherein a difference frequency is selected to be equal to a cross calculation product.

19. A method of spectrographic measurement, comprising the steps of:

(a) generating a plurality of modulation signals at a plurality of modulation frequencies;

(b) coupling said modulation signals to an excitation source, said excitation source producing excitation light for illuminating a sample to assayed, to vary the amplitude of said excitation light by modulating said excitation light with said plurality of modulation signals;

(c) sampling a portion of said excitation light to form a reference optical excitation signal;

(d) illuminating said sample to be assayed with said excitation light, causing said sample to emit an output optical signal;

(e) imaging said output optical signal as an image on an image intensifier;

(f) intensifying said image to form an intensified image;

(g) directing said intensified image on a multielement optical detector having a plurality of elements, whereby each of said elements is associated with a region on said sample to be assayed;

(h) generating a plurality of measurement signals using said multielement optical detector, each measurement signal associated with a single one of said elements;

(i) generating a plurality of heterodyne signals at a plurality of heterodyne frequencies, each of said heterodyne frequencies being associated with one of said modulation frequencies, said heterodyne frequencies being selected to improve resolution of spectrographic measurement;

(j) for each measurement signal associated with an element of said multielement optical detector, mixing said measurement signal with said heterodyne signals to generate a plurality of low-frequency measurement modulation products, one low-frequency measurement modulation product being associated with each of said modulation frequencies and comprising the difference between a respective modulation frequency and its associated heterodyne frequency and having a measurement amplitude and phase;

(k) mixing said reference optical excitation signal with said heterodyne signals to generate a plurality of reference modulation products, one reference modulation product being associated with each of said modulation frequencies and comprising the difference between a single modulation frequency and its associated heterodyne frequency and having a reference amplitude and phase, each of said reference modulation products being associated with one of said low-frequency measurement modulation products; and (l) for each of said plurality of low-frequency measurement modulation products, comparing said low-frequency measurement modulation product to its associated reference modulation product to generate an output signal indicating characteristics of said sample at the region on said sample associated with each of said elements.

* * * * *